United States Patent
Kono et al.

(10) Patent No.: US 10,161,809 B2
(45) Date of Patent: Dec. 25, 2018

(54) METHOD FOR MEASURING INTERNAL TEMPERATURE OF FREEZING TARGET OBJECT AND INTERNAL TEMPERATURE MEASUREMENT DEVICE FOR FREEZING TARGET OBJECT

(71) Applicant: MAYEKAWA MFG. CO., LTD., Tokyo (JP)

(72) Inventors: Shinji Kono, Tokyo (JP); Kazuhiro Hattori, Tokyo (JP)

(73) Assignee: MAYEKAWA MFG. CO., LTD., Tokyo (JP)

( * ) Notice: Subject to any disclaimer, the term of this patent is extended or adjusted under 35 U.S.C. 154(b) by 170 days.

(21) Appl. No.: 15/129,828

(22) PCT Filed: Mar. 12, 2015

(86) PCT No.: PCT/JP2015/057234
§ 371 (c)(1),
(2) Date: Sep. 28, 2016

(87) PCT Pub. No.: WO2015/146600
PCT Pub. Date: Oct. 1, 2015

(65) Prior Publication Data
US 2017/0138801 A1    May 18, 2017

(30) Foreign Application Priority Data

Mar. 28, 2014  (JP) .................................. 2014-068492

(51) Int. Cl.
| | |
|---|---|
| *G01K 11/00* | (2006.01) |
| *G01N 33/02* | (2006.01) |
| *G01K 7/42* | (2006.01) |

(52) U.S. Cl.
CPC .............. *G01K 11/006* (2013.01); *G01K 7/42* (2013.01); *G01K 11/00* (2013.01); *G01N 33/02* (2013.01)

(58) Field of Classification Search
CPC ........ G01K 11/00; G01K 11/006; G01K 7/00; G01N 22/00; G01N 22/02; H05B 6/62
(Continued)

(56) References Cited

U.S. PATENT DOCUMENTS

| | | | |
|---|---|---|---|
| 4,377,733 A * | 3/1983 | Yamaguchi | ............ G01K 1/024 219/516 |
| 2007/0188372 A1* | 8/2007 | Leath | ................... G01K 11/006 342/26 R |
| 2008/0285617 A1 | 11/2008 | Moldover et al. | |

FOREIGN PATENT DOCUMENTS

| | | |
|---|---|---|
| JP | S57-21651 | 5/1982 |
| JP | 2002-532239 | 10/2002 |

(Continued)

OTHER PUBLICATIONS

English Machine translation of WO2012153793.*
(Continued)

*Primary Examiner* — Daniel S Larkin
*Assistant Examiner* — Anthony W Megna Fuentes
(74) *Attorney, Agent, or Firm* — JCIPRNET

(57) ABSTRACT

A method for measuring an internal temperature of a freezing target object includes: a placing step of placing the freezing target object in a microwave resonating magnetic field generated by a microwave resonator; a state detection step of detecting a resonant state of the freezing target object in a frozen state by using the microwave resonator and detecting an internal temperature of the freezing target object by using a temperature meter; a calibration curve calculation step of calculating a calibration curve by performing a regression analysis by using the resonant state as
(Continued)

an explanatory variable and by using the internal temperature of the freezing target object as a response variable; and a temperature calculation step of calculating the internal temperature of the freezing target object in the frozen state by applying the resonant state detected in the detection step to the calibration curve calculated in the calibration curve calculation step.

15 Claims, 16 Drawing Sheets

(58) Field of Classification Search
USPC .................................................. 73/120, 122
See application file for complete search history.

(56) References Cited

FOREIGN PATENT DOCUMENTS

| JP | 2006-266688 | 10/2006 |
|---|---|---|
| WO | 0036880 | 6/2000 |
| WO | 2006004116 | 1/2006 |
| WO | 2012153793 | 11/2012 |

OTHER PUBLICATIONS

"International Preliminary Report on Patentability; this report contains the following items :Form PCT/IB/338, PCT/IB/373, PCT/ISA237(cover sheet), PCT/ISA237(Box No. I),PCT/ISA237(Box No. V)", dated Oct. 13, 2016, which is English translation of "Written Opinion of the International Searching Authority", p. 1-p. 14.

"Search Report of Europe Counterpart Application", dated Feb. 15, 2017, p. 1-p. 7.

Tohi et al., "Control of ice fraction by capacitance measurement for prevention of collapse during freeze drying of food", Journal of the Japanese Society for Food Science and Technology,Aug. 2003, vol. 50, No. 8, pp. 356-360.

Narimiya et al., Summary of "Quality evaluation of food by non-contact capacitive sensor, Part 1: relation between capacitance and temperature of freezing-thawing", Transactions of the Japan Society of Refrigerating and Air Conditioning Engineers, 1999, vol. 16, pp. 1-2.

"International Search Report (Form PCT/ISA/210)", dated Jun. 9, 2015, with English translation thereof, pp. 1-4.

* cited by examiner

METHOD FOR MEASURING INTERNAL TEMPERATURE OF FREEZING TARGET OBJECT AND INTERNAL TEMPERATURE MEASUREMENT DEVICE FOR FREEZING TARGET OBJECT

CROSS-REFERENCE TO RELATED APPLICATION

This application is a 371 of international application of PCT application serial no. PCT/JP2015/057234, filed on Mar. 12, 2015, which claims the priority benefit of Japan Patent Application no. 2014-068492, filed on Mar. 28, 2014. The entirety of each of the abovementioned patent applications is hereby incorporated by reference herein and made a part of this specification.

TECHNICAL FIELD

The present disclosure relates to a method for measuring an internal temperature of a freezing target object for measuring an internal temperature of a freezing target object such as a frozen food product that has been frozen, and an internal temperature measurement device for a freezing target object.

BACKGROUND ART

Management of a process of freezing a frozen food product and the like involves an extremely important task of checking an internal temperature of this freezing target object. Thus, various measurement methods have conventionally been proposed. Such methods include: a method for inserting a temperature sensor in the form of a needle into the freezing target object and measuring the internal temperature; a method for measuring a surface temperature of the freezing target object by an infrared sensor, and a measurement method using change in electric capacity due to change in a physical state of water (see Non-Patent Literature 1 and Non-Patent Literature 2). Another proposed method uses electromagnetic waves in a microwave band to determine whether phase transition of the water content in the freezing target object has occurred (see Patent Literature 1).

When the temperature sensor in the form of a needle is used, the temperature sensor needs to be first inserted in the freezing target object. Thus, when the freezing target object is a solid food product, the inspected food product cannot be delivered to the market to be sold due to the issues of contamination with foreign matters and sanitation attributable to a needle hole remaining at the inserted position. All things considered, the temperature sensor in the form of a needle cannot achieve a 100% inspection of the internal temperature of food products in the process of freezing the food products.

The infrared sensor, which can measure the surface temperature of the freezing target object, cannot measure the internal temperature of the freezing target object, and cannot accurately measure the surface temperature of the food products with a packaging material such as a wrap. The method using the change in the electric capacity, described in Non-Patent Literatures 1 and 2, uses a special measurement device and involves detailed measurement conditions. Thus, the freezing target object is required to be arranged and measured under accurate conditions. Thus, this method is not suitably used for the 100% inspection of the temperature of the food products in the process of freezing the food products.

The method using the electromagnetic waves, described in Patent Literature 1, includes: irradiating an object containing water content with electromagnetic waves at a predetermined frequency emitted from a communication unit; receiving, with a wireless tag, electromagnetic waves, of the electromagnetic waves radiated, which have transmitted through the object; and emitting a response signal from the wireless tag that has received the electromagnetic waves transmitted to the communication unit. The levels of absorption and transmission of the electromagnetic waves in and through the water content largely vary among the phases of the water content that are a liquid phase, a solid phase, and a gaseous phase, that is, among water, ice, and vapor. Thus, the phases distinctively vary from each other in whether the communication unit can communicate with the wireless tag. All things considered, whether the phase transition of the water content has occurred can be determined based on whether the communication unit can communicate with the wireless tag.

CITATION LIST

Patent Literature

[Non-Patent Literature 1] Journal of the Japanese Society for Food Science and Technology, 2003, Vol. 50, No. 8, pp. 356-360
[Non-Patent Literature 2] Transactions of the Japan Society of Refrigerating and Air Conditioning Engineers, 1999, Vol. 16, pp. 23-35
[Patent Literature 1] Japanese Patent Application Laid-open No. 2006-266688

SUMMARY

Technical Problem

With the method for determining whether the phase transition has occurred described in Patent Literature 1, whether the phase transition of the water content in an object has occurred can be determined based on whether the communication unit can communicate with the wireless tag. However, with this method, the temperature in the object is difficult to check. Thus, development of a novel internal temperature measurement method and internal temperature measurement device has been called for, especially for checking the internal temperature of the freezing target object for managing the process of freezing frozen food products and the like that have been frozen.

In view of the above, an object of at least some embodiments of the present invention is to provide a method for measuring an internal temperature of a freezing target object and an internal temperature measurement device for a freezing target object with which an internal temperature of a freezing target object such as a frozen food product that has been frozen with can be measured by using a microwave resonator.

Solution to Problem

A method for measuring an internal temperature of a freezing target object according to some embodiment of the present invention includes: a placing step of placing the freezing target object in a microwave resonating magnetic field generated by a microwave resonator; a state detection step of detecting a resonant state of the freezing target object in a frozen state by using the microwave resonator and detecting an internal temperature of the freezing target object by using a temperature meter; a calibration curve calculation step of calculating a calibration curve by performing a regression analysis by using the resonant state detected in the state detection step as an explanatory variable and by using the internal temperature of the freezing target object detected by the temperature meter as a response variable; and a temperature calculation step of calculating the internal temperature of the freezing target object in the frozen state by applying the resonant state detected in the detection step to the calibration curve calculated in the calibration curve calculation step.

The inventor of the present application has found a correlation between the resonance peak voltage and the internal temperature of the freezing target object, based on a characteristic that the resonance peak voltage and the internal temperature of the freezing target object change in accordance with a change in absorption/transmission of microwaves in and through the freezing target object. The absorption/transmission largely differs between water as a water content in the freezing target object in a liquid phase in the freezing target object and an ice as the water content in a solid phase. Based on this finding, the inventors of the present application have found that by determining the correlation between the resonance peak voltage and the internal temperature of the freezing target object in advance, the internal temperature of the freezing target object corresponding to the resonance peak voltage detected can be calculated as the internal temperature of the freezing target object. Based on this finding, the inventor of the present application has found that the internal temperature of the freezing target object can be estimated from a calibration curve calculated through a regression analysis by using a resonant state of the freezing target object as an explanatory variable and by using the internal temperature of the freezing target object as a response variable. Thus, the internal temperature of the freezing target object in the frozen state can be calculated by applying the resonant state detected in the state detection step to the calibration curve. All things considered, the method for measuring an internal temperature of a freezing target object with which the internal temperature of the freezing target object such as a frozen food product can be measured by using the microwave resonator can be implemented.

In some embodiment, a projection area by the microwave resonator is set to be smaller than a projection area of the freezing target object so that a region of the microwave resonating magnetic field generated by the microwave resonator is encompassed by a region of the freezing target object.

In this configuration, the projection area by the microwave resonator is smaller than the projection area of the freezing target object. Thus, no microwaves, generated by the microwave resonator, are detected without transmitting through the freezing target object. Thus, the detection of the resonant state of the measurement target object can be guaranteed.

In some embodiments, the freezing target object is a solid food product, the resonant state detected in the state detection step is a resonance peak voltage of the freezing target object in the frozen state, and the temperature calculation step includes estimating an internal temperature of the freezing target object in the frozen state by applying the resonance peak voltage detected in the state detection step to the calibration curve calculated in the calibration curve calculation step.

In this configuration, the internal temperature of the solid food product in the frozen state can be estimated by applying the resonance peak voltage detected in the state detection step to the calibration curve.

In some embodiments, the state detection step further includes a resonant frequency detection step of detecting a resonant frequency of the freezing target object by using the microwave resonator, the calibration curve calculation step further includes a frozen state determination step of determining whether the freezing target object is in the frozen state by applying the resonant frequency detected in the resonant frequency detection step to a second calibration curve defining a correlation between the internal temperature and the resonant frequency of the freezing target object, and in the temperature calculation step, the internal temperature of the freezing target object is calculated by applying a detection value indicating the resonance peak voltage at which the freezing target object is determined to be in the frozen state in the frozen state determination step to a first calibration curve defining a correlation between the internal temperature and the resonance peak voltage of the freezing target object.

The inventor of the present application has found a correlation between the resonant frequency and the internal temperature of the freezing target object when the water content is in a phase transition state, based on a characteristic that the resonant frequency and the resonance peak voltage in the microwave resonator change in accordance with a change in absorption/transmission of microwaves in and through the freezing target object. The absorption/transmission largely differs between water as a water content in the freezing target object in a liquid phase in the freezing target object and an ice as the water content in a solid phase. The correlation features the following relationship. Specifically, the internal temperature of the freezing target object remains the same until the resonant frequency reaches a certain value, and gradually decreases once the resonant frequency exceeds the value. Thus, the inventor of the present application has found that the freezing target object is in the frozen state when the resonant frequency is higher than that at the point where the internal temperature starts to gradually decrease, based on the correlation between the resonant frequency and the internal temperature of the freezing target object. In view of this, in the temperature calculation step in the invention according to claim 4, the internal temperature of the freezing target object is calculated by applying a detection value indicating the resonance peak voltage at which the freezing target object is determined to be in the frozen state in the frozen state determination step to a first calibration curve. The internal temperature thus calculated is that of the freezing target object in the frozen state, whereby the internal temperature of the freezing target object in the frozen state can be accurately calculated.

In some embodiments, the solid food product as the freezing target object is a frozen food product conveyed by a conveyer line, the state detection step includes detecting the resonance peak voltage of the frozen food product being conveyed by the conveyer line by using the microwave resonator, and the temperature calculation step includes calculating the internal temperature of the frozen food product being conveyed by the conveyer line.

In this configuration, the freezing target object is a frozen food product conveyed by the conveyer line, the state detection step includes detecting the resonance peak voltage of the frozen food product being conveyed by the conveyer line by using the microwave resonator, and the temperature calculation step includes calculating the internal temperature of the frozen food product being conveyed by the conveyer line. Thus, the 100% of the food product temperature can be achieved for the frozen food products conveyed by the conveyance line, in the process of freezing the frozen food products. All things considered, the internal temperature can be more accurately managed in the process of freezing the frozen food product.

In some embodiments, the state detection step includes detecting the resonance peak voltage of the frozen food product in a non-packed state or in a state of being packed in a microwave transmissible material.

In this configuration, the state detection step includes detecting the resonance peak voltage of the frozen food product in a non-packed state or in a state of being packed in a microwave transmissible material. Thus, the resonance peak voltage can be detected for the frozen food product that has been packed or before being packed. Thus, the resonance peak voltage of the frozen food product can be detected during the process of freezing the frozen food product.

In some embodiments, a thickness of the freezing target object in a microwave radiation direction is equal to or smaller than 50 mm.

In the process of freezing a freezing target object, the inner portion of the freezing target object is more difficult to freeze than its outer side where the freezing starts. Thus, when the internal temperature of the freezing target object can be measured, whether the freezing target object is in the frozen state can be estimated. In view of this, preferably, the thickness of the freezing target object in the microwave radiation direction is equal to or smaller than 50 mm, assuming that the distance required for the microwaves to advance to reach the center portion of the freezing target object in the frozen state is 25 mm. The invention according to claim 7 has a feature that the thickness of the freezing target object in the microwave radiation direction is equal to or smaller than 50 mm. Thus, the microwave can reach the center of the inner portion of the freezing target object, whereby the measurement of the internal temperature of the freezing target object can be guaranteed. Thawing of the freezing target object starts on the outer side of the freezing target object, and ends on its inner side. Once the thawing starts and water is produced on the outer side, the microwaves are absorbed by the water and thus can no longer reach the inner portion of the freezing target object. Thus, the method for measuring an internal temperature according to the present application cannot be applied to a process of thawing a freezing target object.

In some embodiments, the freezing target object is a plurality of small pieces of a frozen food product, the method further comprises a filling step of filling a container with the plurality of pieces of the frozen food product, the resonant state detected in the state detection step is a resonance peak voltage and a resonant frequency of the freezing target object in the frozen state, the temperature calculation step includes estimating an internal temperature of the pieces of the frozen food product in the frozen state by applying the resonance peak voltage and the resonant frequency detected in the state detection step, to the calibration curve calculated in the calibration curve calculation step, and the method further comprises a refilling step of refilling the container containing the plurality of pieces of the food product with the plurality of pieces of the frozen food product to increase a density when a value indicating a level of a correlation between the estimated internal temperature of the pieces of the frozen food product and a measured internal temperature of the pieces of the frozen food product is less than a predetermined value.

In this configuration, the freezing target object is the plurality of small pieces of the frozen food product. The plurality of pieces of the frozen food product has a risk that does not occur with the solid food product. Specifically, the frozen state of the freezing target object might not be detectable when a gap between the small pieces of frozen food product is large, due to the microwave resonator detecting the microwaves that have passed through the gap. Thus, the inventor of the present application further provides the refilling step of refilling the container containing the plurality of pieces of the food product with the plurality of pieces of the frozen food product to increase a density when a value indicating a level of a correlation between the estimated internal temperature of the pieces of the frozen food product and a measured internal temperature of the pieces of the frozen food product is less than a predetermined value. Thus, with no gap between the pieces of the frozen food product, the frozen state of the plurality of pieces of the frozen food product can be detected. All things considered, the method for measuring an internal temperature of a freezing target object with which an internal temperature of a plurality of pieces of frozen food product can be measured by using the microwave resonator can be implemented.

An internal temperature measurement device for a freezing target object according to some embodiments of the present invention includes: a microwave resonator configured to detect a resonant state of the freezing target object in a frozen state; and a temperature calculation unit configured to calculate an internal temperature of the freezing target object in the frozen state by applying the resonant state detected by the microwave resonator to a calibration curve calculated by performing a regression analysis by using the resonant state of the freezing target object in the frozen state as an explanatory variable and the internal temperature of the freezing target object as a response variable. A projection area by the microwave resonator is set to be smaller than a projection area of the freezing target object.

The inventor of the present application has found a correlation between the resonance peak voltage and the internal temperature of the freezing target object, based on a characteristic that the resonant frequency and the resonance peak voltage in the microwave resonator change in accordance with a change in absorption/transmission of microwaves in and through the freezing target object. The absorption/transmission largely differs between water as a water content in the freezing target object in a liquid phase in the freezing target object and an ice as the water content in a solid phase. Based on this finding, the inventors of the present application have found that by determining the correlation between the resonance peak voltage and the internal temperature of the freezing target object in advance, the internal temperature of the freezing target object corresponding to the resonance peak voltage detected can be calculated as the internal temperature of the freezing target object. Based on this finding, the inventor of the present application has found that the internal temperature of the freezing target object can be estimated from a calibration curve calculated through a regression analysis by using a resonant state of the freezing target object as an explanatory variable and by using the internal temperature of the freezing target object as a response variable. Thus, the internal temperature of the freezing target object in the frozen state can be calculated by applying the resonant state detected in the state detection step to the calibration curve. All things considered, the internal temperature measurement device for a freezing target object with which the internal temperature of the freezing target object such as a frozen food product can be measured by using the microwave resonator can be implemented. The projection area by the microwave resonator is smaller than the projection area of the freezing target object. Thus, no microwaves, generated by the microwave resonator, are detected without transmitting through the measurement target object. Thus, the detection of the resonant state of the measurement target object can be guaranteed.

In some embodiments, the freezing target object is a solid food product, the microwave resonator is configured to detect a resonance peak voltage of the freezing target object in the frozen state, and the temperature calculation unit is configured to calculate the internal temperature of the freezing target object in the frozen state by applying the resonance peak voltage detected by the microwave resonator, to a first calibration curve defining a correlation between the internal temperature and the resonance peak voltage of the freezing target object in the frozen state.

In this configuration, the internal temperature of the solid food product can be estimated by applying the resonance peak voltage detected by the microwave resonator to the calibration curve.

In some embodiments, the microwave resonator is configured to detect a resonant frequency of the freezing target object, the internal temperature measurement device further comprises a frozen state determination unit configured to determine whether the freezing target object is in the frozen state by applying the resonant frequency detected by the microwave resonator, to a second calibration curve defining a correlation between the internal temperature and the resonant frequency of the freezing target object, and the temperature calculation unit is configured to calculate the internal temperature of the freezing target object in the frozen state by applying a detection value indicating the resonance peak voltage at which the freezing target object is determined to be in the frozen state by the frozen state determination unit to the first calibration curve.

The inventor of the present application has found a correlation between the resonant frequency and the internal temperature of the freezing target object when the water content is in a phase transitioning state, based on a characteristic that the resonant frequency and the resonance peak voltage in the microwave resonator change in accordance with a change in absorption/transmission of microwaves in and through the freezing target object. The absorption/transmission largely differs between water as a water content in the freezing target object in a liquid phase in the freezing target object and an ice as the water content in a solid phase. The correlation features the following relationship. Specifically, the internal temperature of the freezing target object remains the same until the resonant frequency reaches a certain value, and gradually decreases once the resonant frequency exceeds the value. Thus, the inventor of the present application has found that the freezing target object is in the frozen state when the resonant frequency is higher than that at the point where the internal temperature starts to gradually decrease, based on the correlation between the resonant frequency and the internal temperature of the freezing target object. In view of this, the temperature calculation unit in the invention according to claim 11, calculates the internal temperature of the freezing target object by applying a detection value indicating the resonance peak voltage at which the freezing target object is determined to be in the frozen state in the frozen state determination step to a first calibration curve. The internal temperature thus calculated is that of the freezing target object in the frozen state, whereby the internal temperature of the freezing target object can be accurately calculated.

In some embodiments, the solid food product as the freezing target object is a frozen food product conveyed by a conveyer line, the microwave resonator is configured to detect the resonance peak voltage of the frozen food product being conveyed by the conveyer line, and the temperature calculation unit is configured to calculate the internal temperature of the frozen food product being conveyed by the conveyer line.

In this configuration, the freezing target object is a frozen food product conveyed by the conveyer line, the microwave resonator detects the resonance peak voltage of the frozen food product being conveyed by the conveyer line, and the temperature calculation unit calculates the internal temperature of the frozen food product being conveyed by the conveyer line. Thus, the 100% inspection of the food product temperature can be achieved for the frozen food products conveyed by the conveyance line, in the process of freezing the frozen food products. All things considered, the internal temperature can be more accurately managed in the process of freezing the frozen food product.

In some embodiments, the microwave resonator is configured to detect the resonance peak voltage of the frozen food product in a non-packed state or in a state of being packed in a microwave transmissible material.

In this configuration, the microwave resonator detects the resonance peak voltage of the frozen food product in a non-packed state or in a state of being packed in a microwave transmissible material. Thus, the resonance peak voltage can be detected for the frozen food product that has been packed or before being packed. Thus, the resonance peak voltage of the frozen food product can be detected during the process of freezing the frozen food product.

In some embodiments, the freezing target object is a plurality of small pieces of a frozen food product, the microwave resonator is configured to detect a resonance peak voltage and a resonant frequency of the freezing target object in the frozen state, and the temperature calculation unit is configured to calculate a calibration curve by performing a regression analysis by using the resonance peak voltage and the resonant frequency detected by the microwave resonator as an explanatory variable and the internal temperature of the freezing target object as a response variable, to estimate an internal temperature of the pieces of the frozen food product in the frozen state by applying the resonance peak voltage and the resonant frequency detected by the microwave resonator, to the calibration curve, and to refill a container containing the plurality of pieces of the frozen food product with the plurality of pieces of the frozen food product to increase a density of the plurality of pieces of the frozen food product when a value indicating a level of a correlation between the estimated internal temperature of the individual frozen food products and a measured internal temperature of the individual frozen food products is less than a predetermined value.

In this configuration, the freezing target object is the plurality of small pieces of the frozen food product. The plurality of pieces of the frozen food product has a risk that does not occur with the solid food product. Specifically, the frozen state of the freezing target object might not be detectable when a gap between the small pieces of frozen food product is large, due to the detection of the microwaves that have passed through the gap. Thus, the inventor of the present application further provides a configuration where the container containing the plurality of pieces of the food product is refilled with the plurality of pieces of the frozen food product to increase a density of the plurality of pieces of the food product, when a value indicating a level of a correlation between the estimated internal temperature of the pieces of the frozen food product and a measured internal temperature of the pieces of the frozen food product is less than a predetermined value. Thus, in accordance with a decrease in the gap between the pieces of the frozen food product, concern about the microwaves passing through the gap is steadily eliminated. All things considered, the internal temperature measurement device for a freezing target object with which an internal temperature of a plurality of pieces of frozen food product can be measured by using the microwave resonator can be implemented.

In some embodiments, a thickness of the freezing target object in a microwave radiation direction is equal to or smaller than 50 mm.

In the process of freezing a freezing target object, the inner portion of the freezing target object is more difficult to freeze than its outer side where the freezing starts. Thus, when the internal temperature of the freezing target object can be measured, whether the freezing target object is in the frozen state can be estimated. In view of this, preferably, the thickness of the freezing target object in the microwave radiation direction is equal to or smaller than 50 mm, assuming that the distance required for the microwaves to advance to reach the center portion of the freezing target object in the frozen state is 25 mm. The invention according to claim 15 has a feature that the thickness of the freezing target object in the microwave radiation direction is equal to or smaller than 50 mm. Thus, the microwave can reach the center of the inner portion of the freezing target object, whereby the measurement of the internal temperature of the freezing target object can be guaranteed. Thawing of the freezing target object starts one the outer side of the freezing target object, and ends on its inner side. Once the thawing starts and water is produced on the outer side, the microwaves are absorbed by the water and thus can no longer reach the inner portion of the freezing target object. Thus, the internal temperature measurement device according to the present application cannot be applied to a process of thawing a freezing target object.

Advantageous Effects

With at least some embodiments of the present invention, a method for measuring an internal temperature of a freezing target object and an internal temperature measurement device for a freezing target object can be provided with which the internal temperature of the freezing target object such as a frozen food product that has been frozen can be measured by using a microwave resonator.

DETAILED DESCRIPTION

An embodiment of a method for measuring an internal temperature of a freezing target object and an internal temperature measurement device for a freezing target object according to the present invention will be described below with reference to FIGS. 1 to 19. In the embodiment described below, a method for measuring an internal temperature and an internal temperature measurement device are for a frozen food product as the freezing target object. For example, the frozen food product is a gratin contained in a paper container, and a thickness of the gratin in a microwave radiation direction is equal to or smaller than 50 mm. The frozen food product may also be a food product with starchy sauce, a hamburger steak, a scallop, green peas, or the like packed with resin. Materials, shapes, and relative positional relationships, etc. of components described in the embodiment do not limit the scope of the present invention, and are merely examples used for description. First of all, the internal temperature measurement device for a freezing target object will be described, before the method for measuring an internal temperature of a freezing target object according of the present invention is described.

Figure 1:
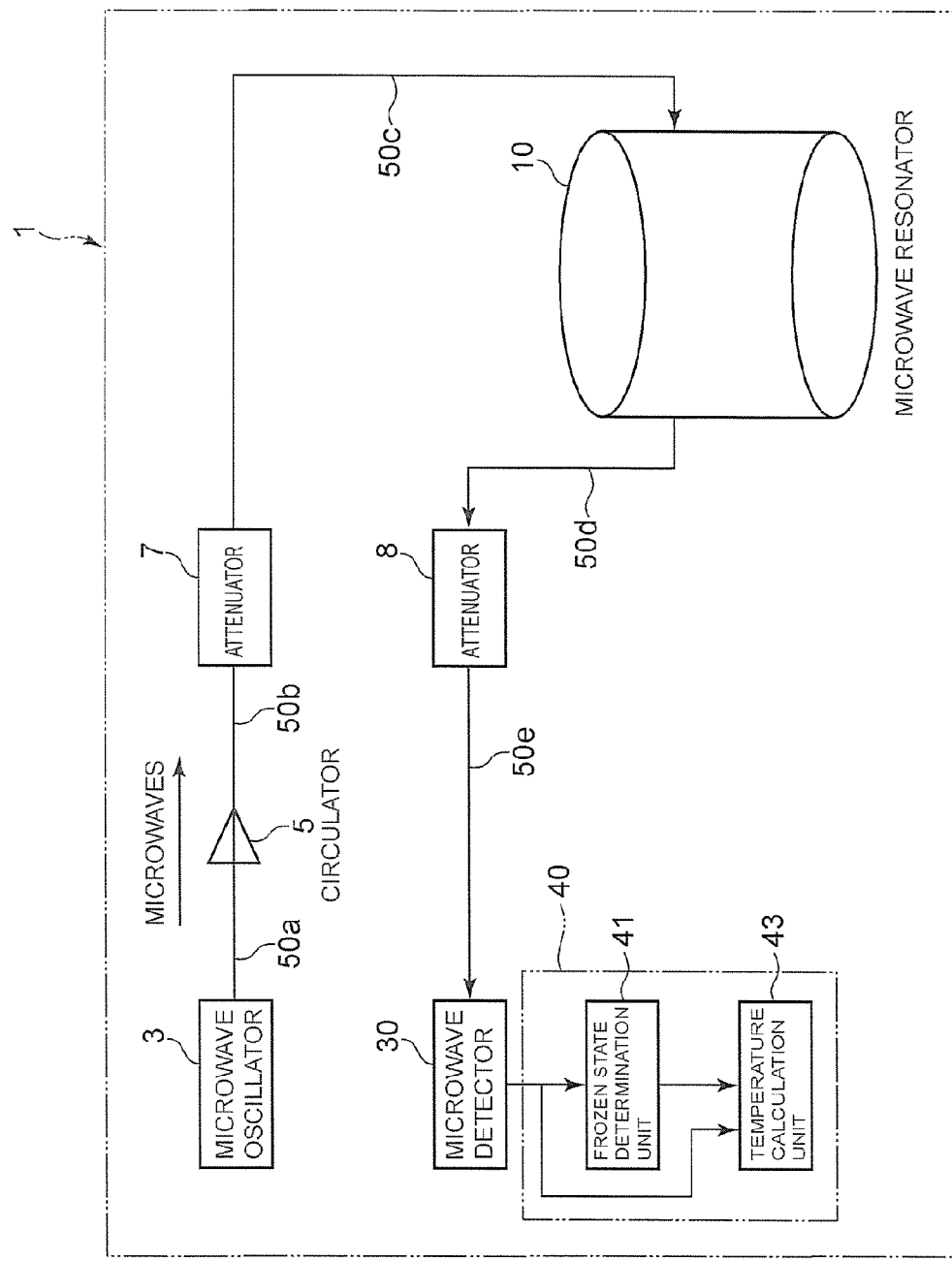
FIG. 1 is a configuration diagram illustrating a configuration of an internal temperature measurement device for a freezing target object according to one embodiment of the present invention.

As illustrated in FIG. 1, an internal temperature measurement device 1 for a freezing target object includes: a microwave oscillator 3 that emits microwaves; a circulator 5; attenuators 7 and 8; a microwave resonator 10 with which a resonant state of the microwaves is achieved; a microwave detector 30 that detects the microwaves; and a data processor 40.

The microwaves emitted from the microwave oscillator 3 are supplied to the circulator 5 through a coaxial cable 50*a*. The circulator 5 has a function of preventing the reflecting microwaves from propagating towards the microwave oscillator 3. Thus, the microwave oscillator 3 is prevented from being damaged by the microwaves emitted from the microwave oscillator 3 and then reflected. The microwaves output from the circulator 5 are supplied to the attenuator 7 through a coaxial cable 50*b*, to have noise removed. The microwaves free of noise are supplied to the microwave resonator 10 through a coaxial cable 50*c*.

Figure 2:
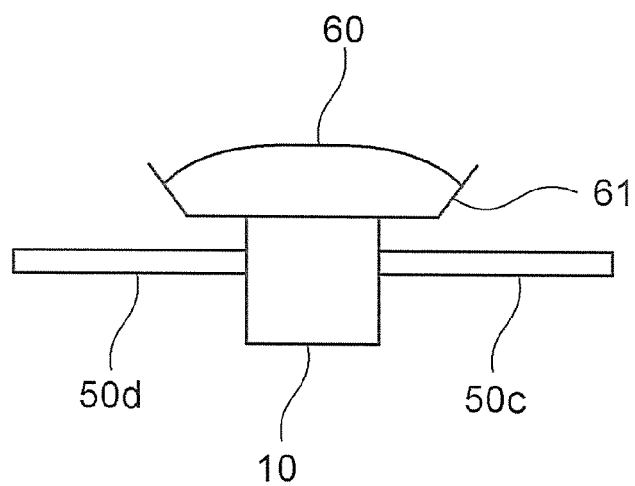
FIG. 2 is a schematic configuration diagram of a microwave cavity resonator that is a part of the internal temperature measurement device.

In the embodiment, as illustrated in FIG. 2, a frozen food product 60 (gratin) contained in a container 61 is placed on the microwave resonator 10. The container 61 is a microwave transmissible container made of paper and in the form of a plate. The container 61 is not limited to the plate form, and may be in the form of a bag that can accommodate the frozen food product 60, or may be a nonmetallic tray.

Figure 3:
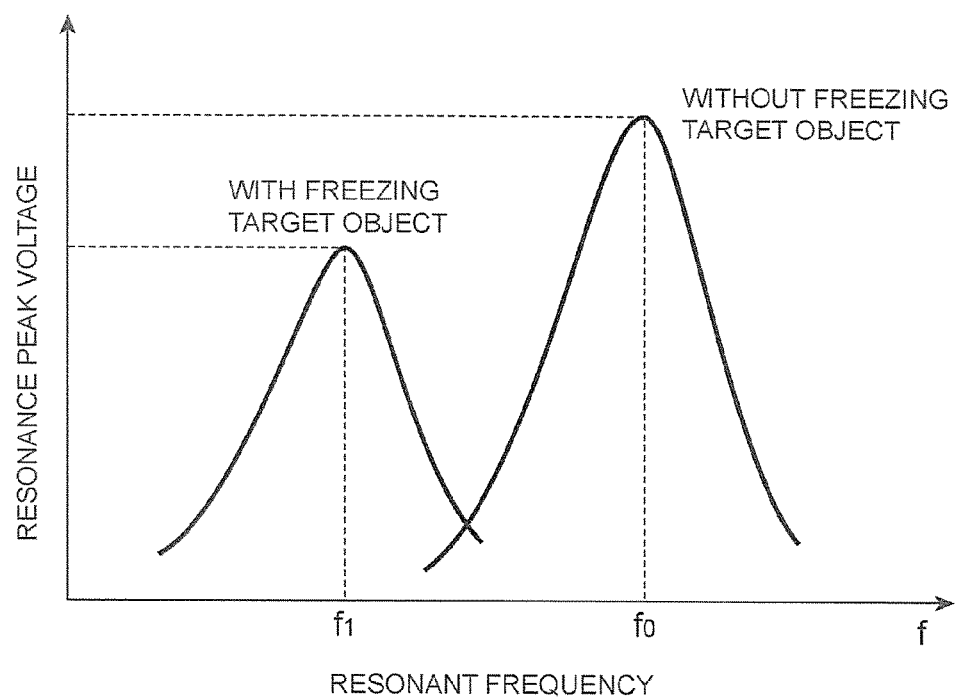
FIG. 3 is a graph illustrating resonation characteristics in cases where a sample is in and not in the microwave cavity resonator.

When the microwaves are introduced into the microwave resonator 10 having the configuration described above, through the coaxial cable 50*c*, the microwaves are reflected in the microwave resonator 10 and resonate at a certain frequency. When the frozen food product 60 is inserted to a microwave resonating magnetic field thus obtained, resonance peak voltage changes and a resonant frequency changes ($f_0 \rightarrow f_1$) as illustrated in FIG. 3. A frozen state and an internal temperature in the frozen food product can be estimated by measuring the microwaves having the resonance peak voltage and the resonance frequency changed, as described in detail later. In FIG. 3, the vertical axis represents the resonance peak voltage and the horizontal axis represents the resonant frequency f.

As illustrated in FIG. 1, the microwaves output from the microwave resonator 10 are supplied to the attenuator 8, through a coaxial cable 50*d*, to have the noise removed. The microwaves free of noise are detected by the microwave detector 30. A detection signal corresponding to the microwaves detected by the microwave detector 30 is transmitted to the data processor 40.

Figure 4:
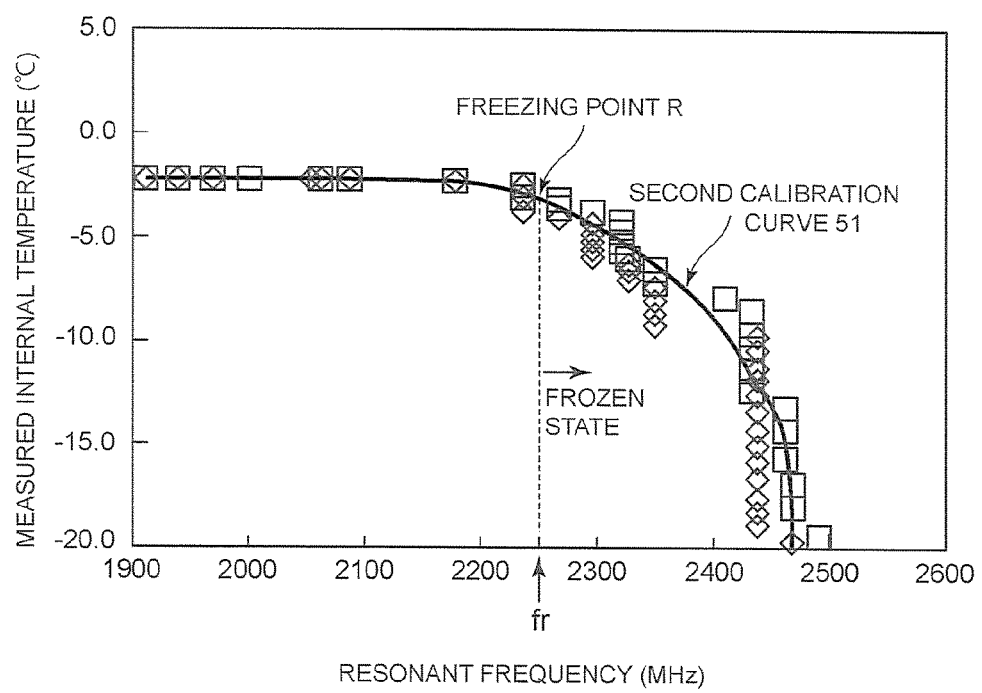
FIG. 4 is a graph illustrating a calibration curve defining a correlation between a measured internal temperature of a freezing target object and a resonant frequency.

The data processor 40 is a computer such as a personal computer for example, and includes a frozen state determination unit 41 and a temperature calculation unit 43. The frozen state determination unit 41 determines whether the freezing target object is in a frozen state, by applying the resonant frequency, detected by the microwave resonator 10 (see FIG. 1), to a second calibration curve 51 that is illustrated in a solid line and representing a correlation between an internal temperature (measured internal temperature) of the freezing target object and the resonant frequency, as illustrated in FIG. 4. Here, the internal temperature of the freezing target object is a measured internal temperature obtained by actually measuring the internal temperature of the freezing target object.

As illustrated in FIG. 4, the internal temperature does not change in accordance with the frequency change until the resonant frequency reaches a range around 2.2 to 2.3 MHz. A sharp temperature change occurring around this range suggests that a latent heat range is exceeded. In other words, it is estimated that the phase transition has occurred when the resonant frequency reaches the range around 2.2 to 2.3 MHz, and this is assumed to be an indicator that can be used for determining whether the phase transition has occurred. Data on the second calibration curve 51 is prepared through measurement on an object that is the same as the freezing target object (frozen food product) as the measured target, and is stored in the data processor 40 (see FIG. 1), before the actual process starts.

The frozen state determination unit 41 (see FIG. 1) determines that the freezing target object is in the frozen state, when the resonant frequency measured is equal to or higher than a resonant frequency fr corresponding to a point (hereinafter, referred to as "freezing point R") at which the resonant frequency starts to change relative to a temperature at which the phase transition of the freezing target object is completed. The frozen state determination unit 41 (see FIG. 1) determines that the freezing target object is in a non-frozen state, when the resonant frequency measured is smaller than the resonant frequency fr corresponding to the freezing point R.

Figure 5:
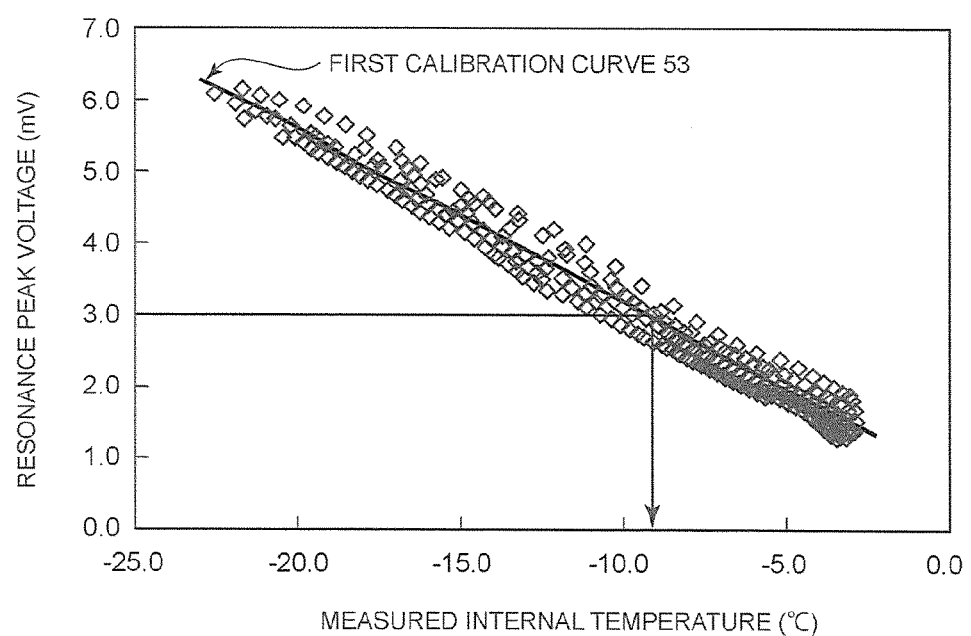
FIG. 5 is a graph illustrating a first calibration curve defining a correlation between a measured internal temperature of a freezing target object in a frozen state and resonance peak voltage.

As illustrated in FIG. 5, the temperature calculation unit 43 (see FIG. 1) applies the resonance peak voltage, detected by the microwave resonator 10, to a first calibration curve 53 defining a correlation between the internal temperature (measured internal temperature) of the freezing target object in the frozen state and the resonance peak voltage, and thus obtains (estimates) the internal temperature of the freezing target object in the frozen state. Here, the internal temperature of the freezing target object in the frozen state is a measured internal temperature obtained by actually measuring the internal temperature of the freezing target object. In FIG. 5, square signs represent measured values of different freezing target objects of the same content (for example, gratin), and a solid line represents the first calibration curve 53. The first calibration curve 53 is set to pass through approximately average values of the plurality of measured values. Data on the first calibration curve 53 is prepared through measurement on an object that is the same as the freezing target object (frozen food product) as the measured target, and is stored in the data processor 40 (see FIG. 1), before the actual process starts. For example, the internal temperature of the freezing target object is measured by an optical fiber thermometer. More specifically, the internal temperature is measured with a distal end portion of the thermometer placed on a center portion of the freezing target object.

The internal temperature of the freezing target object is obtained by applying the resonance peak voltage, detected by the microwave resonator 10, to the first calibration curve 53. For example, when the resonance peak voltage is 3.0 mV, the internal temperature of the freezing target object is estimated to be approximately −9.3° C.

Figure 6:
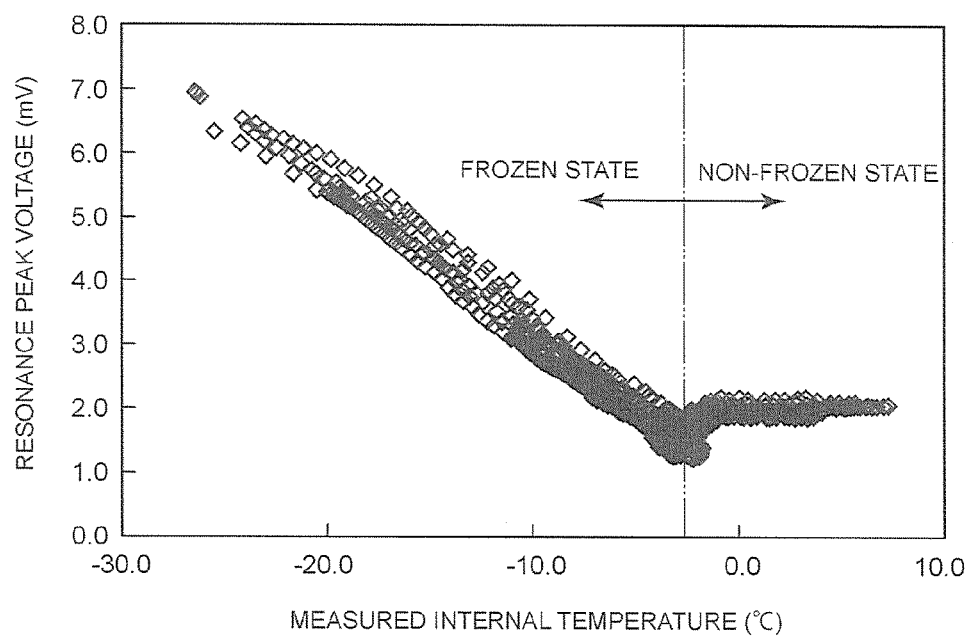
FIG. 6 is a graph illustrating a relationship between a measured internal temperature of the freezing target object in the frozen state and in a non-frozen state and resonance peak voltage.

The inventors of the present application have examined the relationship between the resonance peak voltage and the internal temperature of the freezing target object, based on the following characteristic. Specifically, the resonant frequency and the resonance peak voltage in the microwave resonator change in accordance with a change in absorption/transmission of the microwaves in/through the freezing target object. The absorption/transmission largely differs between water as a water content in the freezing target object in a liquid phase and an ice as the water content in a solid phase. Thus, as illustrated in FIG. 6, the inventor has found that the resonance peak voltage is not correlated with the internal temperature of the freezing target object in the non-frozen state (when the internal temperature is equal to or higher than approximately −2.5° C.) but is correlated with the internal temperature of the freezing target object in the frozen state (when the internal temperature is equal to or lower than approximately −2.5° C.). Based on this finding, the inventor of the present application has found that by determining the correlation between the resonance peak voltage and the internal temperature of the freezing target object in advance, the internal temperature of the freezing target object corresponding to the resonance peak voltage detected can be calculated as the internal temperature of the freezing target object.

Figure 7:
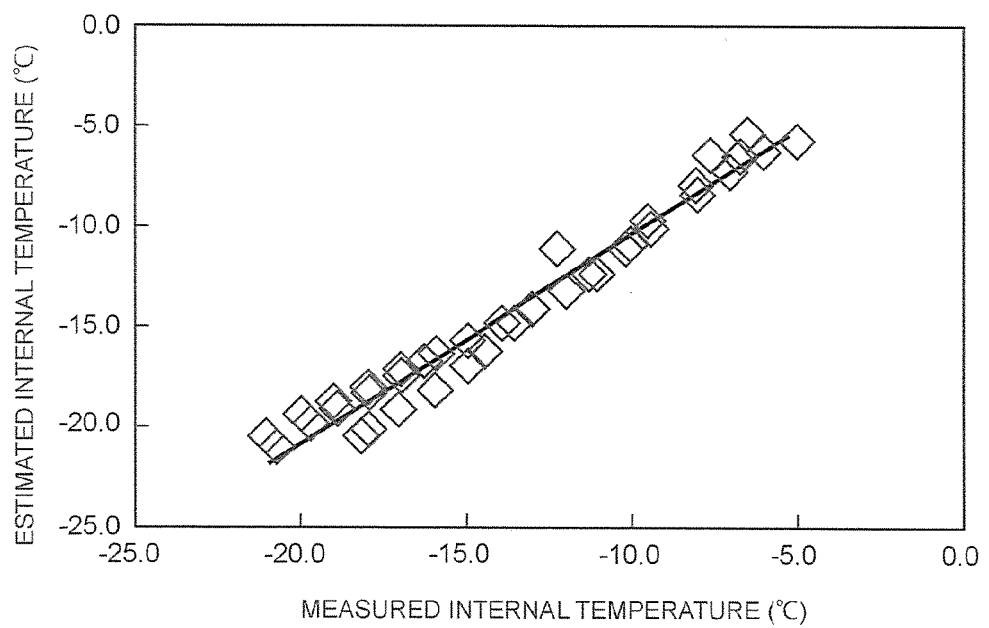
FIG. 7 is a graph illustrating a measured internal temperature of the freezing target object in the frozen state and an estimated internal temperature estimated from the first calibration curve.

FIG. 7 is a graph illustrating an estimated internal temperature and a measured internal temperature. The estimated internal temperature is obtained by estimating the internal temperature of the freezing target object from the resonance peak voltage detected, by using the first calibration curve 53. The measured internal temperature is obtained by actually measuring the actual internal temperature. It can be seen from the graph that the estimated internal temperature and the measured internal temperature approximately match.

Figure 8:
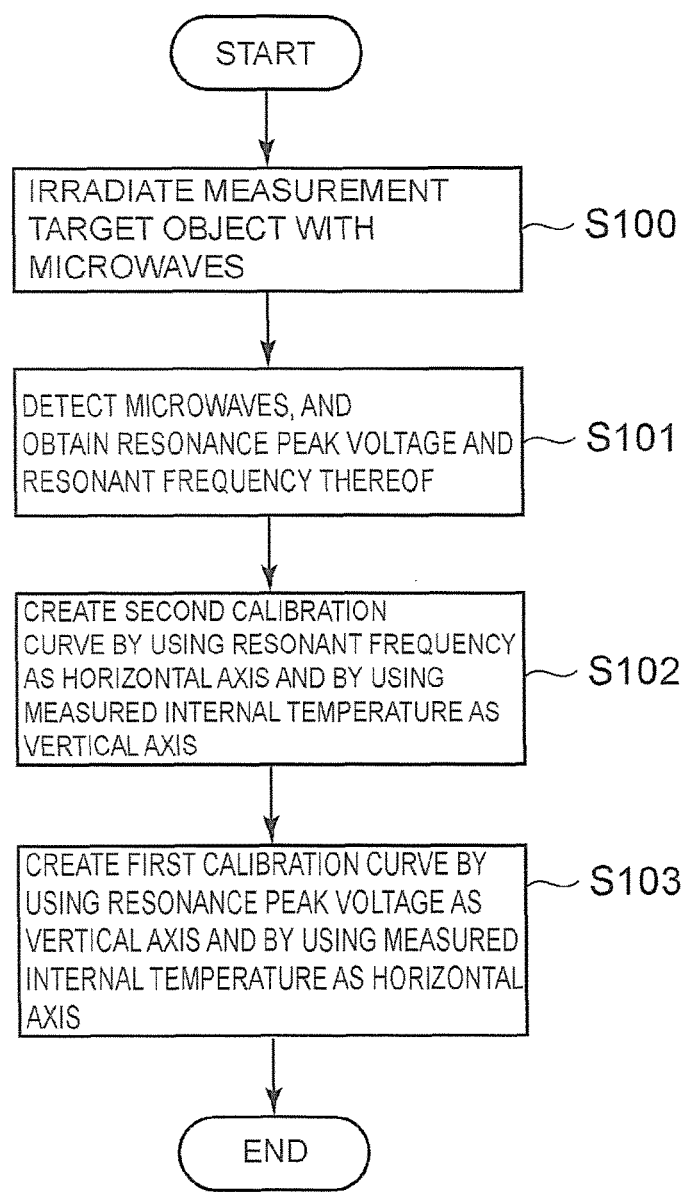
FIG. 8 is a flowchart illustrating processing for obtaining the first calibration curve and a second calibration curve.
Figure 9:
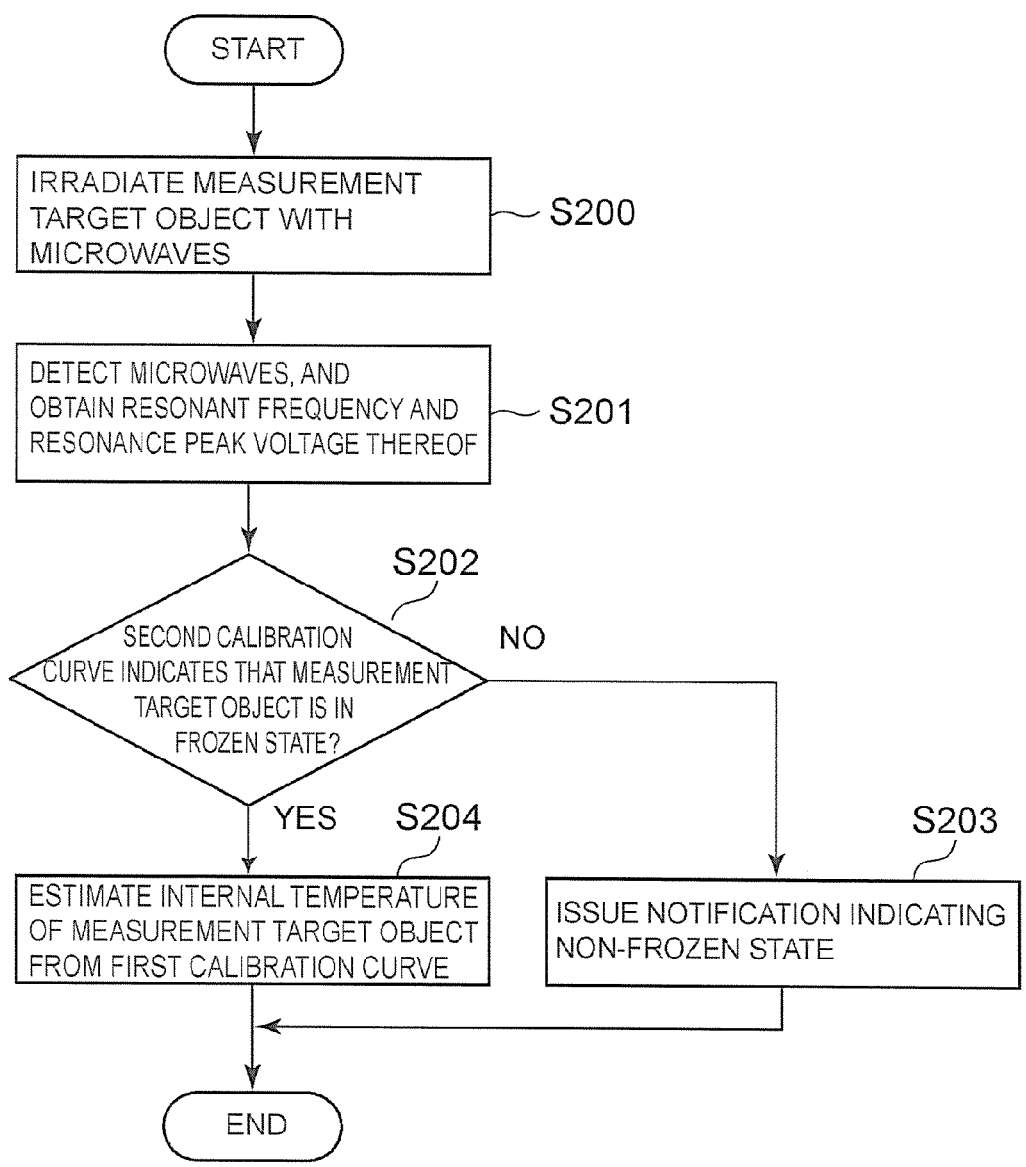
FIG. 9 is a flowchart illustrating processing for obtaining the internal temperature of the freezing target object.

Next, the method for measuring an internal temperature in which the internal temperature measurement device 1 for a freezing target object measures an internal temperature of a freezing target object will be described with reference to FIGS. 8 and 9. First of all, a method for obtaining a first calibration curve and a second calibration curve will be described before the method for measuring an internal temperature of a freezing target object is described. As illustrated in FIGS. 1 and 8, an inspection target object (frozen food product) that is the same as an inspection target object (frozen food product 60) is placed on the microwave resonator 10 and is irradiated with microwaves emitted from the microwave oscillator 3 (step 100).

The microwaves (transmitted waves) radiated on and transmitted through the frozen food product 60 pass through the coaxial cable 50d and a coaxial cable 50e to be detected by the microwave detector 30. An operator or the like obtains the resonance peak voltage and the resonant frequency from the microwaves thus detected (step 101). In step 101, a plurality of the frozen food products 60 are prepared, and for each of the plurality of frozen food products 60, the resonance peak voltage and the resonant frequency are obtained through the method described above and the actual internal temperature is measured. The internal temperature is measured by using, for example, an optical fiber thermometer.

Then, a first calibration curve 52 (see FIG. 4) is created from the resonant frequency and the internal temperature thus obtained (step 102). Specifically, the resonant frequency is used as the horizontal axis and the measured internal temperature is used as the vertical axis. Then, a second calibration curve 51 (see FIG. 5) is created from the resonance peak voltage and the internal temperature thus obtained (step 103). More specifically, the resonance peak voltage is used as the vertical axis and the measured internal temperature is used as the horizontal axis. In the embodiment described above, the second calibration curve 51 is created in step 102 and the first calibration curve 53 is created in step 103. Alternatively, the first calibration curve 53 may be created in step 102, and the second calibration curve 51 may be created in step 103.

Next, the method for measuring an internal temperature of a freezing target object by using the internal temperature measurement device for a freezing target object will be described. As illustrated in FIGS. 1 and 9, the frozen food product 60 (see FIG. 2) is placed on the microwave resonator 10 and is irradiated with the microwaves emitted from the microwave oscillator 3 (step 200).

The microwaves (transmitted waves) radiated on and transmitted through the frozen food product 60 are detected by the microwave detector 30. The operator or the like obtains the resonance peak voltage and the resonant frequency from the microwaves thus detected (step 201). Step 201 is referred to as a resonance peak voltage detection step (state detection step) and a resonant frequency detection step, for the sake of description.

The frozen state determination unit 41 of the data processor 40 applies the resonance peak voltage, obtained in the resonance peak voltage detection step (state detection step) in step 201, to the second calibration curve 51 (see FIG. 4), to determine whether the frozen food product 60 is in the frozen state (step 202, frozen state determination step). When the frozen food product 60 is determined to be in the frozen state in the frozen state determination step, the processing proceeds to step 204. When the frozen food product 60 is determined to be in the non-frozen state in the frozen state determination step, the processing proceeds to step 203 where a notification indicating that the frozen food product 60 is in the non-frozen state is issued. For example, the notification may be displayed on a display unit (not illustrated) provided to the data processor 40, or may be issued through a sound from a speaker (not illustrated) provided to the data processor 40.

When the frozen food product 60 is determined to be in the non-frozen state in the frozen state determination step, the resonance peak voltage, obtained in the resonance peak voltage detection step (state detection step), is applied to the first calibration curve 53, whereby the internal temperature of the frozen food product 60 in the frozen state is obtained (step 204, temperature calculation step). Thus, the internal temperature can be nondestructively estimated with high accuracy without inserting the temperature sensor into the frozen food product 60 in the frozen state.

As described above, the internal temperature of the frozen food product 60 in the frozen state can be calculated by applying the resonance peak voltage, detected in the resonance peak voltage detection step (state detection step), to the first calibration curve 53 defining the correlation between the resonance peak voltage and the internal temperature of the frozen food product 60 in the frozen state. Thus, the method for measuring an internal temperature of a freezing target object can be implemented with which the internal temperature of the freezing target object such as the frozen food product 60 that has been frozen can be measured.

In the temperature calculation step, the internal temperature of the frozen food product 60 is calculated by applying a detection value of the resonance peak voltage, detected when the frozen food product 60 is determined to be in the frozen state in the frozen state determination step, to the first calibration curve 53. Thus, the internal temperature calculated is that of the frozen food product 60 in the frozen state, whereby the internal temperature of the frozen food product 60 in the frozen state can be accurately calculated.

The thickness of the frozen food product 60 (gratin) in the microwave radiation direction is equal to or smaller than 50 mm. Thus, the microwaves can reach the center on an inner side of the frozen food product 60, and can further advance to transmit through the frozen food product 60. Thus, the internal temperature of the frozen food product 60 can be accurately measured.

The frozen food product 60 (gratin) as the freezing target object may be conveyed by a conveyance line. Thus, in the resonance peak voltage detection step (state detection step), the resonance peak voltage may be detected by using the microwave resonator 10 for the frozen food product 60 being conveyed by the conveyance line. In the temperature calculation step, the internal temperature of the frozen food product 60 being conveyed by the conveyance line may be calculated. In such a case, the 100% inspection of the food product temperature can be achieved for the frozen food products conveyed by the conveyance line in the process of freezing the frozen food product 60. Thus, the internal temperature can be managed more accurately in the process of freezing the frozen food product 60.

The microwave resonator 10, which is a microwave cavity resonator in the embodiment described above, may alternatively be a microwave resonator in the form of a probe. Such a microwave resonator emits microwaves while having its distal end portion in contact with the freezing target object, and can receive microwaves radiated on and reflected from the freezing target object.

Figure 10:
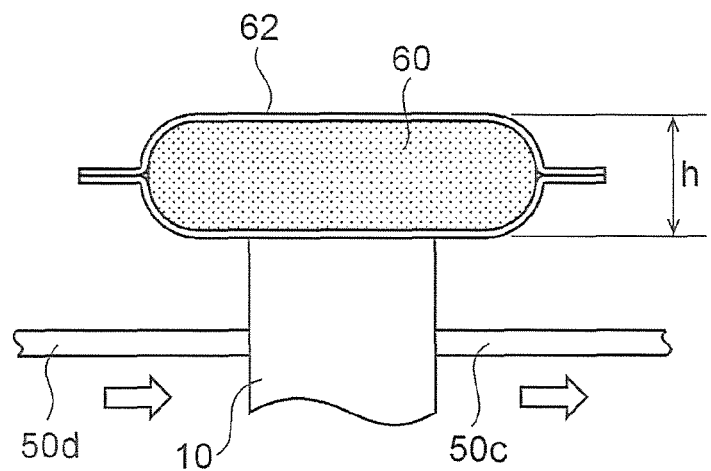
FIG. 10 is a schematic configuration diagram illustrating a state where a frozen food product with starchy sauce covered with a packaging container is placed on a microwave cavity resonator.

The frozen food product 60, which is the gratin contained in the paper container in the embodiment described above, may also be a food product with starchy sauce, a hamburger steak, or a scallop that is packed by a plastic packing material. FIG. 10 illustrates a state where the frozen food product 60 with starchy sauce covered with a nylon packing 62 is placed on the microwave resonator 10. The packing 62 may be made of any microwave transmissible material such as, for example, linear low-density polyethylene, oriented nylon, K-coated nylon, casted nylon, biaxially oriented polypropylene, polyester, and K-coated polyester. The frozen food product 60 with starchy sauce has a size larger than the microwave resonating magnetic field generated by the microwave resonator 10. A length h of the frozen food product 60 with starchy sauce in the height direction is equal to or smaller than 50 mm.

Figure 11:
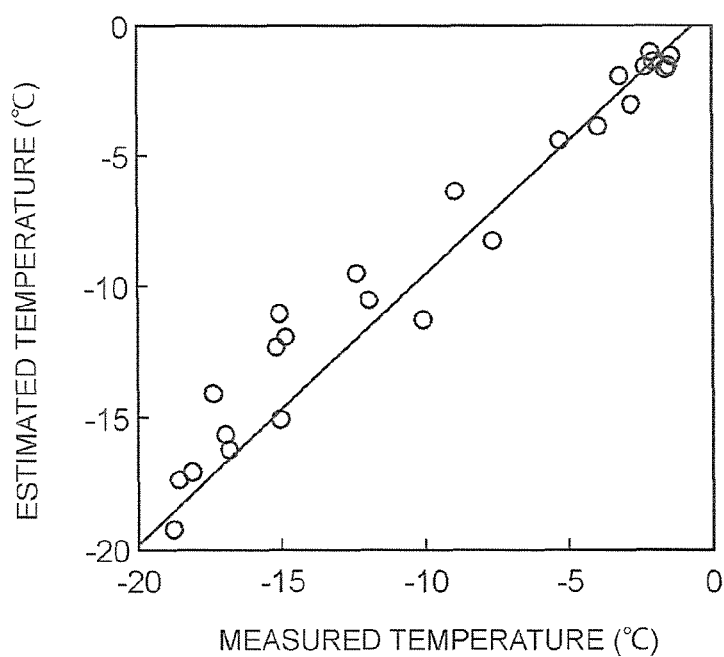
FIG. 11 is a graph illustrating a relationship between a measured internal temperature of the frozen food product with starchy sauce in the frozen state and an estimated internal temperature estimated from the first calibration curve.

FIG. 11 is a graph illustrating a relationship between an estimated internal temperature and a measured internal temperature. The estimated internal temperature is obtained by estimating the internal temperature of the frozen food product 60 (freezing target object) with starchy sauce in a packed state from the resonance peak voltage detected, by using the first calibration curve 53 (see FIG. 5). The measured internal temperature is obtained by actually measuring the actual internal temperature of the frozen food product 60 (freezing target object). It can be seen in the graph that the estimated internal temperature and the measured internal temperature approximately match.

Figure 12:
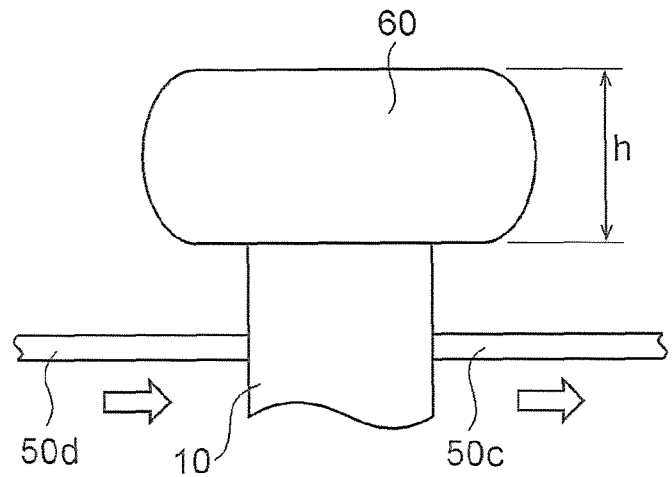
FIG. 12 is a schematic configuration diagram illustrating a state where a hamburger steak as the frozen food product in the frozen state is placed on the microwave cavity resonator.

FIG. 12 illustrates a case where a hamburger steak as the frozen food product 60 in the frozen state is placed on the microwave resonator 10. The hamburger steak as the frozen food product 60 is not packed. The hamburger steak as the frozen food product 60 in the frozen state that is not packed has a size larger than the microwave resonating magnetic field generated by the microwave resonator 10. The hamburger steak as the frozen food product 60 has a length h in the height direction that is equal to or smaller than 50 mm.

Figure 13:
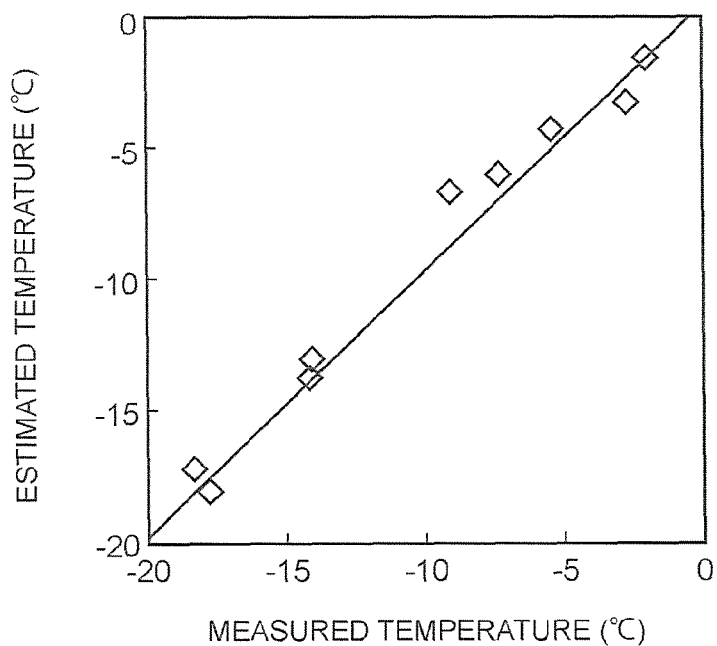
FIG. 13 is a graph illustrating a relationship between the measured temperature of the hamburger steak as the frozen food product in the frozen state and an estimated internal temperature estimated from the first calibration curve.

FIG. 13 is a graph illustrating a relationship between an estimated internal temperature and a measured internal temperature. The estimated internal temperature is obtained by estimating the internal temperature of the hamburger steak as the frozen food product 60 (freezing target object) from the resonance peak voltage detected, by using the first calibration curve 53 (see FIG. 5). The measured internal temperature is obtained by actually measuring the actual internal temperature of the frozen food product 60 (freezing target object). It can be seen in the graph that the estimated internal temperature and the measured internal temperature approximately match.

Figure 14:
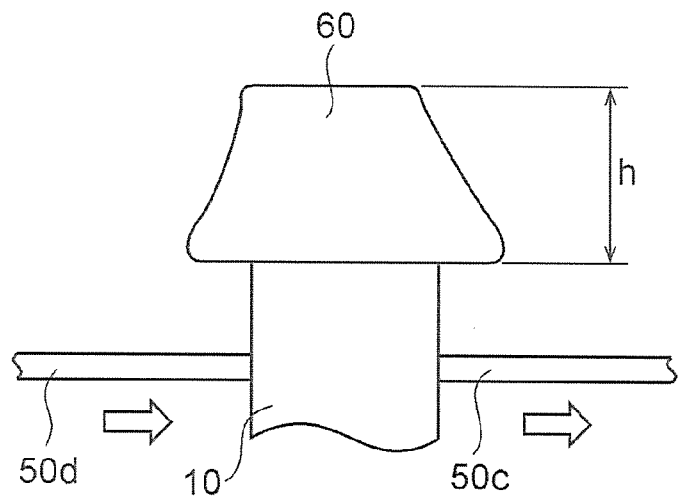
FIG. 14 is a schematic configuration diagram illustrating a state where a scallop as the frozen food in the frozen state is placed on the microwave cavity resonator.

FIG. 14 illustrates a case where a scallop as the frozen food product 60 (freezing target object) in the frozen state is placed on the microwave resonator 10. The scallop as the frozen food product 60 is not packed. The scallop as the frozen food product 60 has a size larger than the microwave resonating magnetic field generated by the microwave resonator 10. The scallop as the frozen food product 60 has a length h in the height direction that is equal to or smaller than 50 mm.

Figure 15:
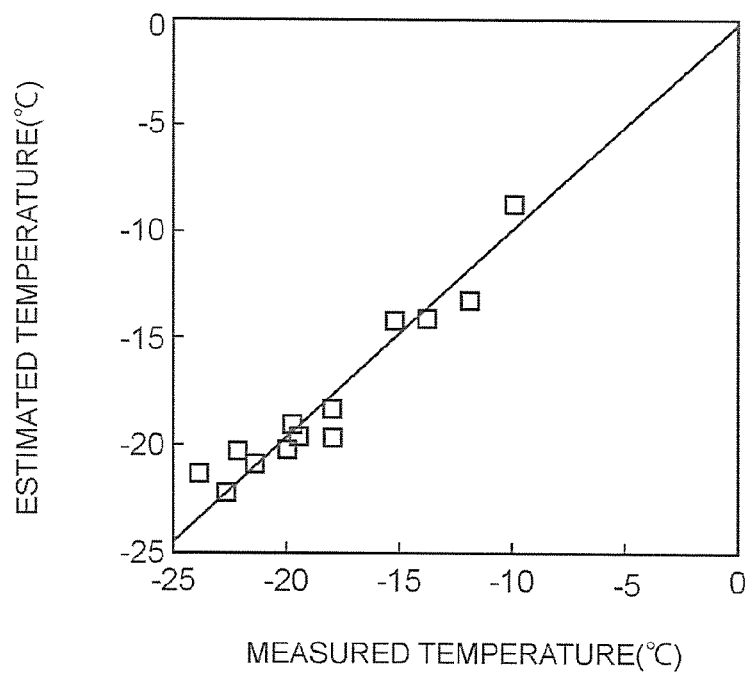
FIG. 15 is a graph illustrating a relationship between a measured internal temperature of the scallop as the frozen food product in the frozen state and an estimated internal temperature estimated from the first calibration curve.

FIG. 15 is a graph illustrating a relationship between an estimated internal temperature and a measured internal temperature. The estimated internal temperature is obtained by estimating the internal temperature of the hamburger steak as the frozen food product 60 (freezing target object) from the resonance peak voltage detected, by using the first calibration curve 53 (see FIG. 5). The measured internal temperature is obtained by actually measuring the actual internal temperature of the hamburger steak as the frozen food product 60. It can be seen in the graph that the estimated internal temperature and the measured internal temperature approximately match.

Figure 16A:
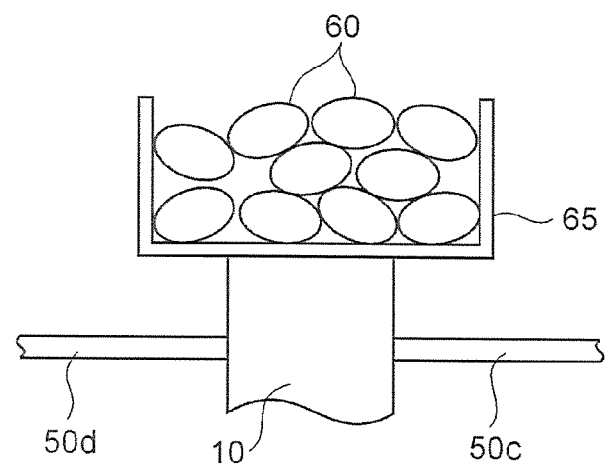
FIG. 16(a) is a schematic configuration diagram illustrating a state where a container filled with a frozen food product in the form of small pieces (small pieces of a frozen product) is placed on the microwave cavity resonator.
Figure 16B:
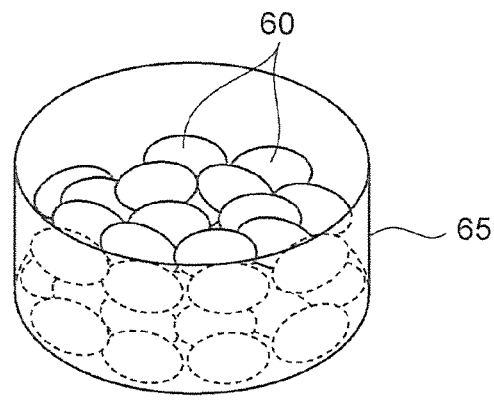
FIG. 16(b) is a schematic configuration diagram illustrating a state where the container is densely filed with the frozen food product in the form of small pieces.
Figure 16C:
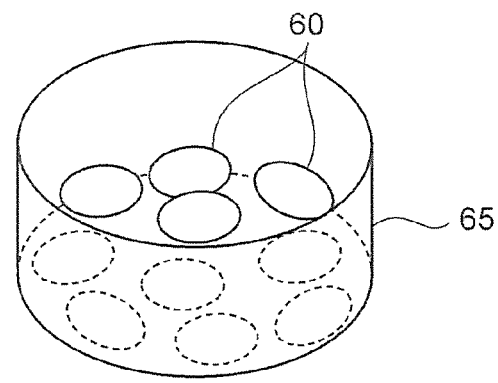
FIG. 16(c) is a schematic configuration diagram illustrating a state where the container is non-densely filled with the frozen food product in the form of small pieces.

FIG. 16(a) illustrates a state where a bottomed container 65, having an upper portion open and containing a plurality of green peas as the frozen food product 60 (freezing target object) in the frozen state, is placed on the microwave resonator 10. The container 65 is made of a microwave transmissible material (such as polyethylene or polyester). Here, the frozen food product 60 (freezing target object) is a plurality of small pieces of frozen food product (green peas). The plurality of green peas as the frozen food product 60 contained in the container 65 have a risk that does not occur with the solid food product such as a gratin or hamburger steak described above. Specifically, when the plurality of green peas as the frozen food product 60 are non-densely contained in the container 65 (see FIG. 16(c)), a gap between the green peas is large. Thus, the frozen state of the green peas as the frozen food product 60 might not be detectable due detection of the microwaves passing through the gap. In view of this, the present inventor has found out how the internal temperature of the green peas as the frozen food product 60 can be estimated. Specifically, a calibration curve can be used that is calculated through a multiple regression analysis in a state where the container 65 is densely filled with the plurality of green peas as the frozen food product 60 (see FIG. 16(*b*)). In the multiple regression analysis, the resonant state (the resonant frequency and the resonance peak voltage) of the green peas as the frozen food product 60 in the frozen state is used as an explanatory variable. The internal temperature of the green peas as the frozen food product 60 in the frozen state is used as a response variable.

Figure 17:
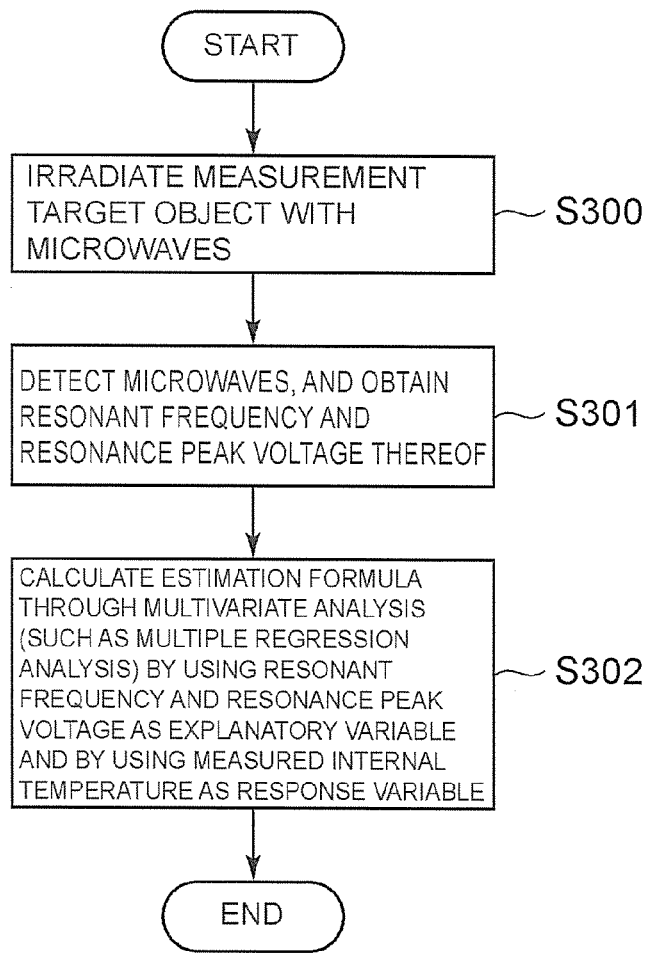
FIG. 17 is a flowchart illustrating processing of obtaining a calibration curve (estimation formula) through a regression analysis.

FIG. 17 is a flowchart illustrating how the calibration curve (estimation formula) is obtained through the multiple regression analysis. As illustrated in FIG. 17, the calibration curve (estimation formula) is obtained as follows. A measurement target object (the green peas as the frozen food product 60) is placed on the microwave resonator 10 and is irradiated with the microwaves emitted from the microwave oscillator 3 (step 300). Here, the container 65 is densely filled with the green peas as the frozen food product 60 as the measurement target object. The projection area by the microwave resonator is smaller than the projection area of the freezing target object, so that no microwaves, generated by the microwave resonator, are detected without transmitting through the measurement target object. Thus, the detection of the resonant state of the measurement target object can be guaranteed.

As illustrated in FIG. 1, the microwave radiated on and transmitted through the frozen food product 60 pass through the coaxial cables 50*d* and 50*e* to be detected by the microwave detector 30. The operator or the like obtains the resonance peak voltage and the resonant frequency from the microwaves thus detected (step 301). In step 301, a plurality of the containers 65 containing the frozen food product 60 (a plurality of green peas) are prepared. For the frozen food product 60 in each of the containers, the resonance peak voltage and the resonant frequency are obtained through the method described above, and the measured internal temperature is measured. The internal temperature is measured, for example, by using an optical fiber thermometer.

Then, the calibration curve (estimation formula) is calculated through the multiple regression analysis by using the resonance peak voltage and the resonant frequency detected by the microwave resonator 10 as the explanatory variable and by using the internal temperature of the freezing target object as the response variable (step 302, calibration curve calculation step).

Figure 18:
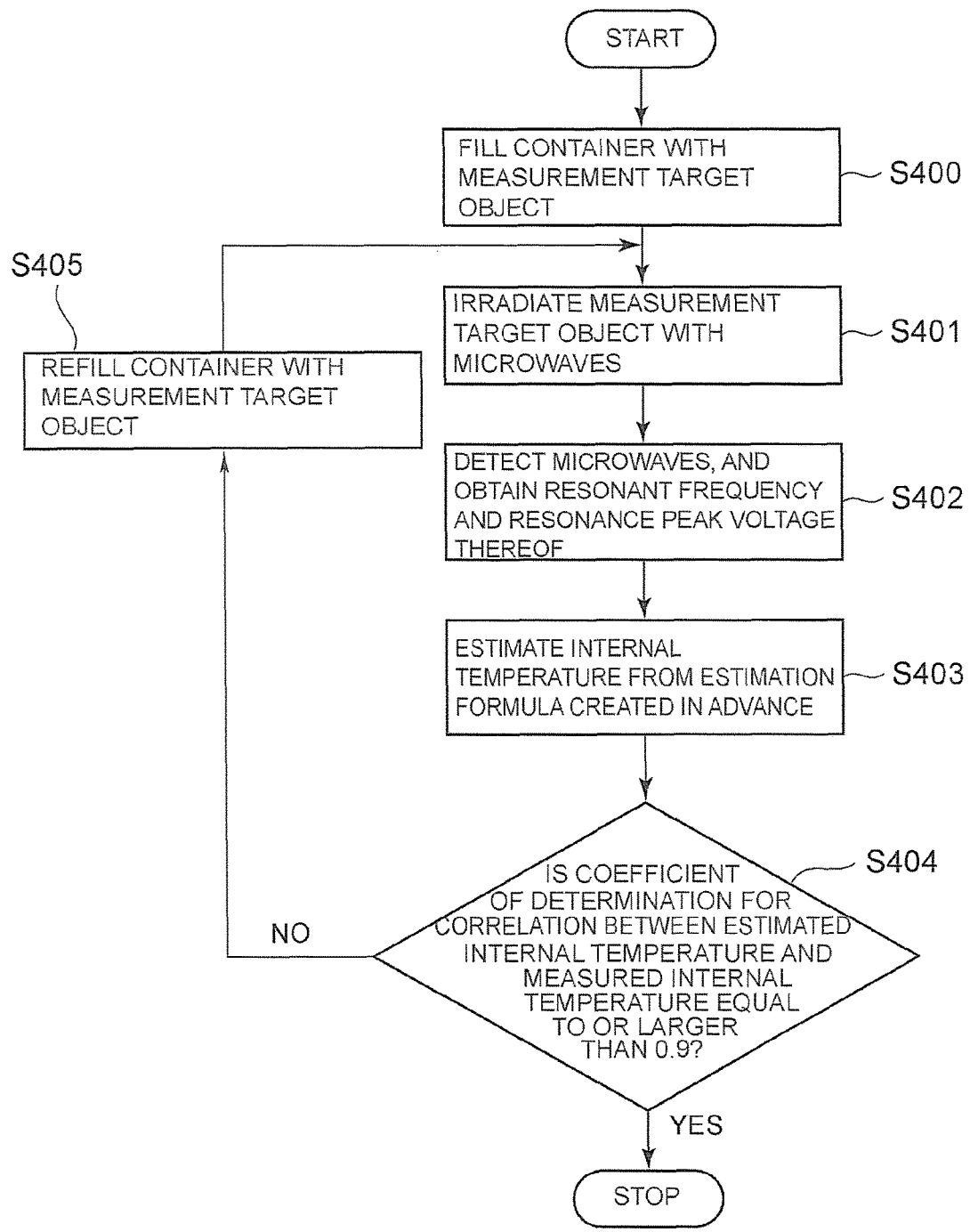
FIG. 18 is a flowchart illustrating processing of obtaining the internal temperature of the frozen food product in the form of small pieces by using the calibration curve (estimation formula) obtained through the regression analysis.

Next, a method for measuring an internal temperature, in which an internal temperature of a measurement target object is measured based on the calibration curve (estimation formula) calculated through the multiple regression analysis, is described with reference to FIG. 18. The container 65 is filled with the plurality of green peas as the frozen food product 60 in the frozen state (see FIG. 2) (step 400, filling step). Then, the container 65 is placed on the microwave resonator 10, and the plurality of green peas as the frozen food product 60 in the microwave resonator 10 are irradiated with the microwaves emitted from the microwave oscillator 3 (step 401, placing step).

The microwaves (transmitted waves) radiated on and transmitted through the plurality of green peas as the frozen food product 60 are detected by the microwave detector 30. The operator or the like obtains the resonance peak voltage and the resonant frequency from the microwaves thus detected (step 402, state detection step, resonant frequency detection step).

Then, the resonance peak voltage and the resonant frequency thus detected are applied to the calibration curve (estimation formula) described above, whereby the internal temperature of the frozen food product 60 is estimated (step 403, temperature calculation step). The container 65 is refilled with the plurality of small pieces of food product to increase the density of the small pieces of food product in the container 65 containing the plurality of small pieces of food product (step 405, refilling step), when a value (for example a coefficient of determination $R^2$) indicating the level of correlation between the estimated internal temperature and the measured internal temperature, estimated and measured for the small pieces of frozen food product, is smaller than a predetermined value (for example, coefficient of determination $R^2=0.9$) (step 404). More specifically, the container 65 is provided with vibrations and the like to be densely filled with the small pieces of frozen food product. Then, the processing in and after step 401 is executed.

Figure 19:
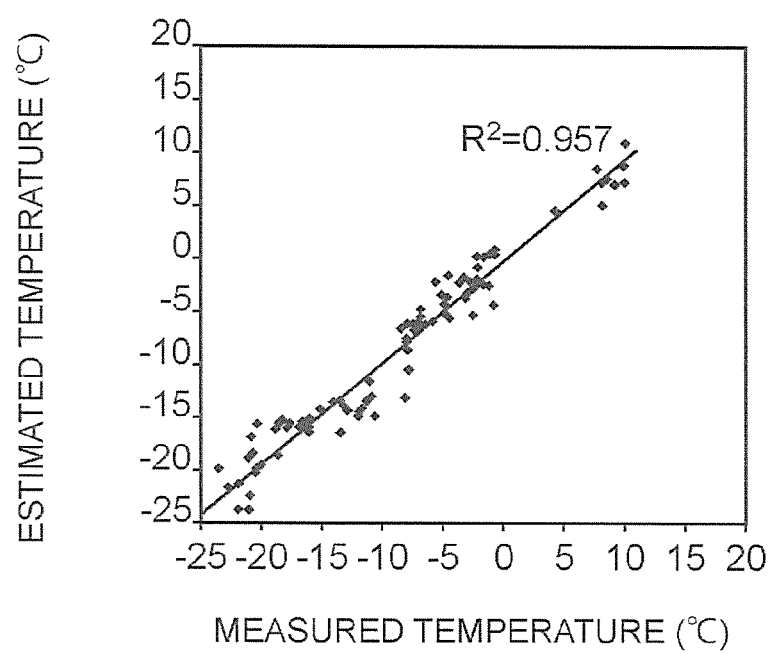
FIG. 19 is a graph illustrating a relationship between the measured internal temperature of the frozen food product in the form of small pieces in the frozen state and an estimated internal temperature estimated from the first calibration curve.

FIG. 19 is a graph illustrating a relationship between the estimated internal temperature and the measured temperature. The estimated internal temperature is obtained by estimating the internal temperature of the frozen food product 60 (green peas) in the frozen state through the multiple regression analysis. The measured internal temperature is obtained by actually measuring the actual internal temperature of the freezing target object.

It can be seen from the graph that the estimated internal temperature and the measured temperature approximately match (the coefficient of determination $R^2=0.957$).

As described above, in the state where the plurality of pieces of frozen food product (for example, green peas) are contained, the internal temperature of the small pieces of frozen food product can be estimated with high accuracy.

The internal temperature of the frozen gratin may be estimated by using the regression analysis. In such a case, the calibration curve is calculated through the regression analysis by using the resonance peak voltage of the gratin as the explanatory variable and by using the internal temperature of the gratin as the response variable. Then, the internal temperature of the grating can be estimated by applying the resonance peak voltage detected to the calibration curve.

The present invention is not limited to the embodiments of the present invention described above, and can be modified in various ways without departing from the object of the present invention. For example, the various embodiments described above may be combined as appropriate.

The invention claimed is:

1. A method for measuring an internal temperature of a freezing target object, the method comprising:
 a placing step of placing the freezing target object in a microwave resonating magnetic field generated by a microwave resonator;
 a state detection step of detecting a resonant state of the freezing target object in a frozen state by using the microwave resonator;
 a temperature calculation step of calculating the internal temperature of the freezing target object in the frozen state by at least applying a resonance peak voltage obtained from the resonant state detected in the state detection step to a calibration curve calculated by performing a regression analysis in which the internal temperature of the freezing target object is a response variable and a resonance peak voltage of an inspection target object whose constituent is the same as the freezing target object is included as an explanatory variable, the resonance peak voltage of the inspection target object being detected using the microwave resonator.

2. The method for measuring an internal temperature of a freezing target object according to claim 1, wherein
a projection area by the microwave resonator is set to be smaller than a projection area of the freezing target object so that a region of the microwave resonating magnetic field generated by the microwave resonator is encompassed by a region of the freezing target object.

3. The method for measuring an internal temperature of a freezing target object according to claim 1, wherein
the freezing target object is a solid food product,
the resonant state detected in the state detection step is a resonance peak voltage of the freezing target object in the frozen state, and
the temperature calculation step includes: estimating an internal temperature of the freezing target object in the frozen state by applying the resonance peak voltage detected in the state detection step to the calibration curve.

4. The method for measuring an internal temperature of a freezing target object according to claim 3, wherein
the state detection step further includes: a resonant frequency detection step of detecting a resonant frequency of the freezing target object by using the microwave resonator,
wherein the method further comprises: a frozen state determination step of determining whether the freezing target object is in the frozen state by applying the resonant frequency detected in the resonant frequency detection step to a second calibration curve defining a correlation between the internal temperature and the resonant frequency of the freezing target object, and
in the temperature calculation step, the internal temperature of the freezing target object is calculated by applying a detection value indicating the resonance peak voltage at which the freezing target object is determined to be in the frozen state in the frozen state determination step to a first calibration curve defining a correlation between the internal temperature and the resonance peak voltage of the freezing target object.

5. The method for measuring an internal temperature of a freezing target object according to claim 3, wherein
the solid food product as the freezing target object is a frozen food product conveyed by a conveyer line,
the state detection step includes: detecting the resonance peak voltage of the frozen food product being conveyed by the conveyer line by using the microwave resonator, and
the temperature calculation step includes: calculating the internal temperature of the frozen food product being conveyed by the conveyer line.

6. The method for measuring an internal temperature of a freezing target object according to claim 5, wherein
the state detection step includes: detecting the resonance peak voltage of the frozen food product in a non-packed state or in a state of being packed in a microwave transmissible material.

7. The method for measuring an internal temperature of a freezing target object according to claim 1, wherein
a thickness of the freezing target object in a microwave radiation direction is equal to or smaller than 50 mm.

8. The method for measuring an internal temperature of a freezing target object according to claim 1, wherein the freezing target object is a plurality of pieces of a frozen food product, the method further comprises: a filling step of filling a container with the plurality of pieces of the frozen food product, the resonant state detected in the state detection step is a resonance peak voltage and a resonant frequency of the freezing target object in the frozen state, the temperature calculation step includes: estimating the internal temperature of the pieces of the frozen food product in the frozen state by applying the resonance peak voltage and the resonant frequency detected in the state detection step, to the calibration curve, and the method further comprises: a refilling step of refilling the container containing the plurality of pieces of the food product with the plurality of pieces of the frozen food product to increase a density of the plurality of pieces of the frozen food product when a value indicating a level of a correlation between the estimated internal temperature of the pieces of the frozen food product and a measured internal temperature of the pieces of the frozen food product is less than a predetermined value.

9. An internal temperature measurement device for a freezing target object, the device comprising:
a microwave resonator, configured to detect a resonant state of the freezing target object in a frozen state; and
a temperature calculation unit, configured to calculate an internal temperature of the freezing target object in the frozen state by at least applying a resonance peak voltage obtained from the resonant state detected by the microwave resonator to a calibration curve calculated by performing a regression analysis in which the internal temperature of the freezing target object is a response variable and a resonance peak voltage of an inspection target object whose constituent is the same as the freezing target object is included as an explanatory variable, the resonance peak voltage of the inspection target object being detected using the microwave resonator,
wherein a projection area by the microwave resonator is set to be smaller than a projection area of the freezing target object.

10. The internal temperature measurement device for a freezing target object according to claim 9, wherein
the freezing target object is a solid food product,
the microwave resonator is configured to detect a resonance peak voltage of the freezing target object in the frozen state, and
the temperature calculation unit is configured to calculate the internal temperature of the freezing target object in the frozen state by applying the resonance peak voltage detected by the microwave resonator, to a first calibration curve defining a correlation between the internal temperature and the resonance peak voltage of the freezing target object in the frozen state.

11. The internal temperature measurement device for a freezing target object according to claim 10, wherein
the microwave resonator is configured to detect a resonant frequency of the freezing target object,
the internal temperature measurement device further comprises: a frozen state determination unit, configured to determine whether the freezing target object is in the frozen state by applying the resonant frequency detected by the microwave resonator, to a second calibration curve defining a correlation between the internal temperature and the resonant frequency of the freezing target object, and
the temperature calculation unit is configured to calculate the internal temperature of the freezing target object in the frozen state by applying a detection value indicating the resonance peak voltage at which the freezing target object is determined to be in the frozen state by the frozen state determination unit to the first calibration curve.

12. The internal temperature measurement device for a freezing target object according to claim 10, wherein
the solid food product as the freezing target object is a frozen food product conveyed by a conveyer line,
the microwave resonator is configured to detect the resonance peak voltage of the frozen food product being conveyed by the conveyer line, and
the temperature calculation unit is configured to calculate the internal temperature of the frozen food product being conveyed by the conveyer line.

13. The internal temperature measurement device for a freezing target object according to claim 12, wherein
the microwave resonator is configured to detect the resonance peak voltage of the frozen food product in a non-packed state or in a state of being packed in a microwave transmissible material.

14. The internal temperature measurement device for a freezing target object according to claim 9, wherein
the freezing target object is a plurality of pieces of a frozen food product,
the microwave resonator is configured to detect a resonance peak voltage and a resonant frequency of the freezing target object in the frozen state, and
the temperature calculation unit is configured to calculate a calibration curve by performing a regression analysis by using the resonance peak voltage and the resonant frequency detected by the microwave resonator as an explanatory variable and the internal temperature of the freezing target object as a response variable, to estimate an internal temperature of the pieces of the frozen food product in the frozen state by applying the resonance peak voltage and the resonant frequency detected by the microwave resonator, to the calibration curve, and to refill a container containing the plurality of pieces of the frozen food product with the plurality of pieces of the frozen food product to increase a density of the plurality of pieces of the frozen food product when a value indicating a level of a correlation between the estimated internal temperature of the individual frozen food products and a measured internal temperature of the individual frozen food products is less than a predetermined value.

15. The internal temperature measurement device for a freezing target object according to claim 9, wherein
a thickness of the freezing target object in a microwave radiation direction is equal to or smaller than 50 mm.

* * * * *